(12) United States Patent
Gillessen et al.

(10) Patent No.: US 7,947,293 B2
(45) Date of Patent: May 24, 2011

(54) AQUEOUS PHARMACEUTICAL FORMULATION

(75) Inventors: Dieter Gillessen, Pratteln (CH); Juergen Jaeger, Reinach (CH)

(73) Assignee: Arpida AG, Reinach (CH)

( * ) Notice: Subject to any disclaimer, the term of this patent is extended or adjusted under 35 U.S.C. 154(b) by 311 days.

(21) Appl. No.: 12/099,284

(22) Filed: Apr. 8, 2008

(65) Prior Publication Data

US 2009/0253722 A1 Oct. 8, 2009

(51) Int. Cl.
*A61K 9/00* (2006.01)
*A01N 43/54* (2006.01)
*C07D 405/06* (2006.01)

(52) U.S. Cl. .......... 424/400; 514/275; 540/480
(58) Field of Classification Search .......... None
See application file for complete search history.

(56) References Cited

U.S. PATENT DOCUMENTS 5,773,446 A * 6/1998 Masciadri .......... 514/275

FOREIGN PATENT DOCUMENTS

| JP | 76-021996 | * | 7/1976 |
| WO | WO 97/20839 A1 | | 6/1997 |
| WO | WO 2005/014857 A1 | | 2/2005 |
| WO | WO 2006/087143 A1 | | 8/2006 |

OTHER PUBLICATIONS

English Equivalent Abstract for JP 76-021996.*
Remington: The Science and Practice of Pharmacy (1995); pp. 1540-1543.*
J. Andrews et al.; "Concentrations in plasma, epithelial lining fludi, alveolar macropages and bronchial mucosa after a single intravenous dose of 1.6 mg/kg of iclaprim (AR-100) in healthy men"; Journal of Antimicrobial Chemotherapy (2007), vol. 60, No. 3, Sep. 2007, pp. 677-680.
International Search Report for International Application No. PCT/EP2008/054232, date mailed Feb. 4, 2009.
Written Opinion of the International Searching Authority of International Application No. PCT/EP2008/054232.
P. Hadvary, A. Leighton, M. Wargenau, T. Thomsen, and K. Islam, "Evaluation of the Effect of Iclaprim on the QT Interval in Healthy Volunteers", Oct. 5, 2007.

* cited by examiner

*Primary Examiner* — Robert A Wax
*Assistant Examiner* — Jeffrey T Palenik
(74) *Attorney, Agent, or Firm* — Dickstein Shapiro LLP

(57) ABSTRACT

The invention concerns a stable aqueous pharmaceutical composition comprising 5-[(2RS)-2-cyclopropyl-7,8-dimethoxy-2H-1-benzopyran-5-ylmethyl]-pyrimidine-2,4-diamine in form of the water soluble methanesulfonic acid salt, a physiological sodium chloride solution, ethanol and Povidone 12 PF, the liquid having a pH of over and above 4.8, but not higher than 5.2, and wherein the oxygen amount is controlled to be 0.8 ppm or less; which can be sterilized by filtration and/or by heated treatment, stored for longer time periods and which can be use for bolus injection or diluted for i.v. infusion.

21 Claims, No Drawings

AQUEOUS PHARMACEUTICAL FORMULATION

The present invention relates to a stable aqueous pharmaceutical composition comprising 5-[(2RS)-2-cyclopropyl-7,8-dimethoxy-2H-1-benzopyran-5-ylmethyl]-pyrimidine-2,4-diamine known as iclaprim.

Iclaprim is a novel diaminopyrimidine antibiotic with a potent activity against a broad spectrum of Gram-positive bacteria, including MRSA (methicillin-resistant *Staphylococcus aureus*). It is also active against several important Gram-negative and intracellular pathogens. Iclaprim exhibits a rapid bactericidal efficacy and is therefore able to actively kill pathogens, rather than just stopping their growth. Furthermore, it was shown to penetrate well into tissues (such as for instance skin, soft tissues and lungs) that often harbor difficult to treat bacterial pathogens.

This new class of diaminopyrimidine antibiotics including iclaprim is described in U.S. Pat. No. 5,773,446 in the unit dosage forms of tablets, coated tablets, dragees, hard and soft gelatine capsules, solutions, emulsions or suspensions. It is further reported in U.S. Pat. No. 5,773,446 that the solutions, emulsions or suspensions may be administered rectally, e.g. in the form of suppositories, or parenterally, e.g. in the form of injection solutions, without however providing any details as to the composition of said solutions. The example given in U.S. Pat. No. 5,773,446 relates to a tablet formulation comprising 4-[5-(2,4-diamino-pyrimidin-5-ylmethyl)-8-methoxy-2H-1-benzopyran-7-yloxy]-butyric acid in combination with sulfamethoxazole. Formulations in form of a solution, particularly a solution comprising 5-[(2RS)-2-cyclopropyl-7,8-dimethoxy-2H-1-benzopyran-5-ylmethyl]-pyrimidine-2,4-diamine, are not exemplified.

Some of the salts of 5-[(2RS)-2-cyclopropyl-7,8-dimethoxy-2H-1-benzopyran-5-ylmethyl]-pyrimidine-2,4-diamine are water soluble and it was therefore to be expected that preparation of aqueous pharmaceutical compositions containing, for example, the methanesulfonic acid salt can be easily accomplished. When preparing an aqueous pharmaceutical composition containing 5-[(2RS)-2-cyclopropyl-7,8-dimethoxy-2H-1-benzopyran-5-ylmethyl]-pyrimidine-2,4-diamine in form of the methanesulfonic acid salt, it was however surprisingly found that the aqueous formulation was not stable. This was not to be expected, since the iclaprim salt in form of solid substance was stable even under stressed conditions.

For example, when the 5-[(2RS)-2-cyclopropyl-7,8-dimethoxy-2H-1-benzopyran-5-ylmethyl]-pyrimidine-2,4-diamine methanesulfonic acid salt was prepared as an aqueous 30% propylene glycol or in 10% glycofurol solution, these aqueous standard formulations encountered severe stability problems under simulated long term storage conditions.

Similar standard formulations were also studied for their stability under simulated sterilization conditions, where they again showed severe stability problems which were further increased when the pH of the solution was adjusted to a pH of below 3.5.

Furthermore, precipitation of the 5-[(2RS)-2-cyclopropyl-7,8-dimethoxy-2H-1-benzopyran-5-ylmethyl]-pyrimidine-2,4-diamine methanesulfonic acid salt in saline was observed when the concentration of 5-[(2RS)-2-cyclopropyl-7,8-dimethoxy-2H-1-benzopyran-5-ylmethyl]-pyrimidine-2,4-diamine was increased above 7.5 mg/mL in saline solutions such as, for example, a 10% propylene glycol saline solution.

There was therefore a desire for improved formulations in form of a concentrated (stock) solution which can be sterilized by methods known in the art such as filtration and/or heat sterilization and, allow long term storage without changes of the parent compound or formation of by-products. The so formulated stock solution can be suitably used for direct injection as a bolus or as i.v. infusion after dilution with appropriate injectable solutions.

It was, therefore, one of the objectives of the present invention to prepare a concentrated (stock) solution of 5-[(2RS)-2-cyclopropyl-7,8-dimethoxy-2H-1-benzopyran-5-ylmethyl]-pyrimidine-2,4-diamine acid addition salt such as, for example, methanesulfonic acid salt, which may be used as such or, prior to use, may be diluted with normal saline for parenteral administration.

It was a further objective of the invention to provide a concentrated (stock) solution, the components of which are stable for an extended period of time, particularly between 1 month and at least 24 months, and which can be conditioned in containers such as vials or ampoules which have the advantage of easy storage and shipping.

In accordance with the present invention it has been surprisingly found that excluding or substantially excluding oxygen from the aqueous concentrated solution considerably improves the chemical stability of iclaprim. It has further been found that iclaprim remains freely soluble and stable in physiologically acceptable solutions if the pH of the solution is maintained in a range of between about pH 4.2 to about pH 5.7.

The present invention therefore now provides a composition comprising a stable aqueous solution, particularly a concentrated (stock) stable aqueous solution, of iclaprim consisting essentially of a physiologically acceptable solution of 5-[(2RS)-2-cyclopropyl-7,8-dimethoxy-2H-1-benzopyran-5-ylmethyl]-pyrimidine-2,4-diamine (iclaprim) acid addition salt characterized in that said solution is free or essentially free of oxygen.

In one embodiment of the invention, the oxygen content of the solution is 0.8 ppm or less.

In one embodiment of the invention the, the oxygen content of the solution is less than 0.8 ppm.

In one embodiment, the composition according to the invention and as described herein before comprises a 5-[(2RS)-2-cyclopropyl-7,8-dimethoxy-2H-1-benzopyran-5-ylmethyl]-pyrimidine-2,4-diamine (iclaprim) acid addition salt selected from the group of salts consisting of a salt with a mineral acid, an organic sulfonic acid and an organic carboxylic acid, separately and mixtures thereof.

In one embodiment, the composition according to the invention and as described herein before comprises a 5-[(2RS)-2-cyclopropyl-7,8-dimethoxy-2H-1-benzopyran-5-ylmethyl]-pyrimidine-2,4-diamine (iclaprim) acid addition salt with a mineral acid, particularly a mineral acid selected from the group consisting of hydrohalic acids such as hydrochloric acid, hydrogen bromide and hydrogen iodide, sulphuric acid, nitric acid, phosphoric acid and the like, separately and mixtures thereof.

In one embodiment, the composition according to the invention and as described herein before comprises a 5-[(2RS)-2-cyclopropyl-7,8-dimethoxy-2H-1-benzopyran-5-ylmethyl]-pyrimidine-2,4-diamine (iclaprim) acid addition salt with an organic sulfonic acid, particularly an alkyl- and arylsulfonic acid, particularly an alkyl- and arylsulfonic acid selected from the group consisting of methanesulfonic acid, p-toluene-sulfonic acid, benzenesulfonic acid and the like, separately and mixtures thereof.

In one embodiment, the composition according to the invention and as described herein before comprises a 5-[(2RS)-2-cyclopropyl-7,8-dimethoxy-2H-1-benzopyran-5-ylmethyl]-pyrimidine-2,4-diamine (iclaprim) acid addition salt with an organic carboxylic acid, particularly an organic carboxylic acid selected from the group consisting of acetic acid, tartaric acid, maleic acid, citric acid, benzoic acid, salicylic acid, ascorbic acid and the like, separately and mixtures thereof.

In one embodiment, a composition according to the invention is provided as described herein before, wherein the pH of the solution is in a range of between pH 4.0 and pH 5.9, particularly in a range of between pH 4.2 and pH 5.7, particularly in a range of between pH 4.4 and pH 5.5, particularly in a range of between pH 4.6 and pH 5.2, particularly in a range of between pH 4.9 and pH 5.1, but especially in a range of between pH 4.8 and pH 5.2.

In order to adjust the pH in a range below pH 4.5, the composition according to the invention and as described herein before may contain a physiologically acceptable acid, particularly an inorganic mineral acid selected from the group consisting of hydrochloric, hydrobromic, sulphuric, phosphoric, nitric acid and the like, or an organic acid selected from the group consisting of acetic, succinic, tartaric, ascorbic, citric, glutamic, benzoic, methanesulfonic, ethanesulfonic acid and the like, separately and mixtures thereof.

In one embodiment, the pH adjustment may be accomplished in the composition according to the invention and as described herein before by a physiologically acceptable acidic buffer solution, particularly a buffer solution selected from the group of citric buffer, acetate buffer, phosphate buffer and the like, separately and mixtures thereof.

In order to adjust the pH in a range above pH 4.5, the composition according to the invention and as described herein before may contain a physiologically acceptable alkalinizing agent, particularly an agent selected from the group of sodium hydroxide, mono-, di-, and triethanolamine, and the like, separately and mixtures thereof.

In one embodiment, the pH adjustment may be accomplished in the composition according to the invention and as described herein before by a physiologically acceptable buffer solution, particularly a alkali buffer solution selected from the group of phosphate buffer, TRIS buffer, and the like, separately and mixtures thereof.

In one embodiment, a composition according to the invention is provided as described herein before, wherein the physiologically acceptable solvent is water or an organic solvent selected from the group consisting of alcohol, a physiological saline, an aliphatic amine, a glycol, a polyalcohol, esters of a polyalcohol, polyglycols, polyethers, and sugar alcohols or mixtures thereof.

In one embodiment of the invention, the physiologically acceptable solvent is a mixture of water and organic solvents, particularly a mixture containing from about 100% to about 40%, particularly from about 95% to about 55%, particularly from about 80% to about 65%, by volume of water.

In one embodiment of the invention, the physiologically acceptable solvent is water.

In one embodiment of the invention, the physiologically acceptable organic solvent is ethanol.

In one embodiment, the composition according to the invention and as described herein before comprises a co-solubilizing agent, particularly a co-solubilizing agent selected from the group consisting of polyethylene glycols, propylene glycol, Triacetin, ethanol, polyethylene glycol, esters of fatty acids, propylene glycol esters of fatty acids, glycerin, oleic acid, and the like, separately and mixtures thereof.

In one embodiment, the composition according to the invention and as described herein before comprises a physiologically acceptable inorganic chloride, particularly sodium chloride.

In one embodiment of the invention, the physiologically acceptable inorganic chloride, particularly the sodium chloride, is present in the aqueous solution in a concentration of between 0% and 3%, particularly in a concentration of between 0.1% and 2.5%, particularly in a concentration of between 0.2% and 2.0%, particularly in a concentration of between 0.5% and 1.5%, particularly in a concentration of between 0.6% and 1%.

In one embodiment, a composition according to the invention is provided as described herein before, wherein the concentration of the 5-[(2RS)-2-cyclopropyl-7,8-dimethoxy-2H-1-benzopyran-5-ylmethyl]-pyrimidine-2,4-diamine (iclaprim) in the solution is in a range of at least 0.1% (w/w), particularly in a range of at least 0.5% (w/w), particularly in a range of at least 1.0% (w/w), particularly in a range of at least 2.0% (w/w), particularly in a range of at least 5.0% (w/w), particularly in a range of at least 8.0% (w/w).

In a specific embodiment of the invention, the concentration of the 5-[(2RS)-2-cyclopropyl-7,8-dimethoxy-2H-1-benzopyran-5-ylmethyl]-pyrimidine-2,4-diamine (iclaprim) in the solution is in a range of at least 1% but not exceeding 2%.

In one embodiment, the composition according to the invention and as described herein before further comprises a physiologically acceptable carrier and/or excipient including, for example, a wetting agent, particularly a wetting agent selected from the group consisting of N-methylpyrrolidone, polyvinylpyrrolidones such as, for example, Povidone 12 PF, Povidone 17 PF, Povidone 25, Povidone 30, Povidone 90 F, cyclodextrin such as, for example, 2-hydroxypropyl-$\beta$-cyclodextrin, macrogol hydroxystearate, and macrogol glycerol ricinoleate.

In one embodiment of the invention, the concentration of the wetting agent is in the range of between 0% and 20%, particularly in the range of between 0.5% and 15%, particularly in the range of between 1% and 10%, particularly in the range of between 6.5% and 9.5%, but especially in a range of between 5% and 10%.

In one embodiment of the invention, a composition is provided comprising a stable aqueous solution of iclaprim consisting essentially of a physiologically acceptable solvent, particularly a mixture of water and ethanol, particularly a mixture of water and ethanol containing from about 100% to about 40%, particularly from about 95% to about 55%, particularly from about 80% to about 65%, by volume of water, a physiologically acceptable inorganic chloride, particularly sodium chloride, particularly a sodium chloride in a concentration of between 0% and 3%, particularly in a concentration of between 0.1% and 2.5%, particularly in a concentration of between 0.2% and 2.0%, particularly in a concentration of between 0.5% and 1.5%, particularly in a concentration of between 0.6% and 1%, a physiologically acceptable wetting agent, particularly a polyvinylpyrrolidone such as, for example, Povidone 12 PF, Povidone 17 PF, Povidone 25, Povidone 30, Povidone 90 F, particularly in a concentration range of between 0.5% and 15%, particularly in the range of between 1% and 10%, particularly in the range of between 6.5% and 9.5%, but especially in the range of between 5% and 10%, and a 5-[(2RS)-2-cyclopropyl-7,8-dimethoxy-2H-1-benzopyran-5-ylmethyl]-pyrimidine-2,4-diamine (iclaprim) acid addition salt, particularly the 5-[(2RS)-2-cyclopropyl-7,8-dimethoxy-2H-1-benzopyran-5-ylmethyl]-pyrimidine-2,4-diamine (iclaprim) methanesulfonic acid addition salt, particularly in a concentration of at least 0.1% (w/w), particularly in a range of at least 0.5% (w/w), particularly in a range of at least 1.0% (w/w), particularly in a range of at least 2.0% (w/w), particularly in a range of at least 5.0% (w/w), particularly in a range of at least 8.0% (w/w), but especially in a range of at least 1% but not exceeding 2%, wherein said solution is free or essentially free of oxygen, particularly has an oxygen concentration of 0.8 ppm or less and wherein the pH of the solution is in a range of between pH 4.0 and pH 5.9, particularly in a range of between pH 4.2 and pH 5.7, particularly in a range of between pH 4.4 and pH 5.5, particularly in a range of between pH 4.6 and pH 5.2, particularly in a range of between pH 4.9 and pH 5.1, but especially in a range of between pH 4.8 and pH 5.2.

In one embodiment, the composition according to the invention and as described herein above is provided as a stock solution, particularly as a concentrated stock solution, for long term storage and easy shipping.

In one embodiment, said stock solution is a water solution.

In one embodiment, the composition according to the invention and as described herein above is provided as a ready-to-use injection solution for bolus injection.

In one embodiment, the composition according to the invention and as described herein above is provided as a ready-to-use injection solution, wherein a stock solution as described herein above is complemented and completed to the desired volume with a physiologically acceptable solute selected from the group consisting of injectable water, a glucose solution, a full electrolyte solution containing or not amino acids, lipids, vitamins, traces elements and other minerals, a Ringer-lactate solution, a Ringer-acetate solution, a sodium chloride solution in form of an isotonic, hypotonic or hypertonic solution.

In one embodiment of the invention, a composition is provided as described herein before, which comprises a further biologically active agent or compound, particularly a pharmaceutically active agent or compound, particularly a further antimicrobial compound, particularly an antibacterial compound.

In one embodiment, the composition comprises a further antibacterial compound, particularly an antibacterial compound that acts as an inhibitor of enzymes which are involved in folic acid biosynthesis, particularly a compound that exhibits a synergistic effect when administered in combination with iclaprim, particularly a sulfonamide or a pteridine derivative, particularly a sulfonamide selected from the group consisting of sulfamethoxazole, sulfisoxazole, sulfadimethoxine, dapsone.

A further aspect of the invention relates to the provision of the composition according to the invention and as described herein above in a suitable packaging for long time storage and/or parenteral administration.

In one embodiment, the invention provides a container, particularly a sealed container, particularly a vial or an ampoule comprising the composition according to the invention and as described herein above.

In one embodiment of the invention, said container is a plastic or a glass container.

In one embodiment of the invention, said container comprises the composition according to the invention and as described herein above comprising a physiologically acceptable solution, which is free or essentially free of oxygen and an oxygen concentration in the headspace of less than 5% (v/v), particularly of less than 4% (v/v), but especially of less than 3% (v/v).

In one embodiment of the invention, said glass container is a sealed glass vial or ampoule, particularly a sealed glass vial or ampoule with a total volume of between 5 mL and 10 mL, particularly between 5 mL and 8 mL, particularly between 5.5 mL and 6.5 mL.

The invention also provides a process for producing a composition comprising a stable aqueous solution, particularly a concentrated stable aqueous solution, of iclaprim consisting essentially of a physiologically acceptable solvent and a 5-[(2RS)-2-cyclopropyl-7,8-dimethoxy-2H-1-benzopyran-5-ylmethyl]-pyrimidine-2,4-diamine (iclaprim) acid addition salt characterized in that said solution is free or essentially free of oxygen, which process comprises dissolving a 5-[(2RS)-2-cyclopropyl-7,8-dimethoxy-2H-1-benzopyran-5-ylmethyl]-pyrimidine-2,4-diamine (iclaprim), particularly a physiologically acceptable acid addition salt thereof, in a physiologically acceptable solvent therefor; removing the oxygen from the solution to obtain a solution that is free or essentially free of oxygen, particularly a solution with an oxygen concentration of 0.8 ppm or less; and sterilizing the composition.

In one embodiment of the invention, the oxygen may be removed from the solution by purging the solution with nitrogen.

In one embodiment, a process is provided as described herein above which comprises the additional step of adjusting the pH within the desired range of between pH 4.0 and pH 5.9, particularly in a range of between pH 4.2 and pH 5.7, particularly in a range of between pH 4.4 and pH 5.5, particularly in a range of between pH 4.6 and pH 5.2, particularly in a range of between pH 4.9 and pH 5.1, but especially in a range of between pH 4.8 and pH 5.2.

In one embodiment of the invention, the pH may be adjusted to the desired range as indicated above by adding a physiologically acceptable acid and/or an alkalinizing agent and/or a buffer as disclosed herein before.

In one embodiment, the process according to the invention and as described herein before comprises the additional step of adding further ingredients such as a physiologically acceptable excipient and/or a physiologically acceptable inorganic chloride of the kind as previously specified herein.

In one embodiment of the invention, sterilization of the composition according the invention and as described herein above is accomplished by passing the solution through a sterile filter.

In one embodiment of the invention, sterilization of the composition according the invention is accomplished by subjecting the solution to high temperatures, particularly to a temperature of between 100° C. and 175° C., particularly between 115° C. and 160° C., and high pressure, particularly to a pressure in the range of between 997 mbar and 2900 mbar particularly of between 1600 mbar and 2500 mbar for a defined period of time, particularly for a period of time in the range of between 5 minutes and 2 hours, particularly of between 10 minutes and 30 minutes.

In one embodiment of the invention, sterilization of the composition according the invention is accomplished by subjecting the solution to a combined sterile filtration and a high temperature/high pressure regime as described above.

In one embodiment, the invention provides a process for the production of a ready-to-use injection solution, particularly a ready-to-use injection solution for bolus injection.

In one embodiment, the invention provides a process for the production of a ready-to-use injection solution, particularly a ready-to-use injection solution for infusion, which process comprises diluting a stock solution according to the invention and as described herein previously with a physiologically acceptable solute selected from the group consisting of injectable water, a glucose solution, a full electrolyte solution containing or not amino acids, lipids, vitamins, traces elements and other minerals, a Ringer-lactate solution, a Ringer-acetate solution, a sodium chloride solution in form of a isotonic, hypotonic or hypertonic solution until the desired volume is reached.

In one embodiment, the invention provides a process for the production of a container particularly a sealed container, particularly a vial or an ampoule comprising the composition according to the invention and as described herein above, which process comprises the steps of
 a) mixing of water and the constituents of the composition such as, for example, a physiologically acceptable organic solvent, a physiologically acceptable inorganic chloride, a physiologically acceptable wetting agent, under conditions excluding or substantially excluding oxygen, for example in a nitrogen atmosphere, until complete dissolution,
 b) followed by the addition of 5-[(2RS)-2-cyclopropyl-7,8-dimethoxy-2H-1-benzopyran-5-ylmethyl]-pyrimidine-2,4-diamine methanesulfonic acid salt until complete dissolution,
 c) followed by the adjustment of the pH to the desired range of between pH 4.0 and pH 5.9, particularly in a range of between pH 4.2 and pH 5.7, particularly in a range of between pH 4.4 and pH 5.5, particularly in a range of between pH 4.6 and pH 5.2, particularly in a range of between pH 4.9 and pH 5.1, but especially in a range of between pH 4.8 and pH 5.2,
 d) followed by the sterile filtration, particularly filtration under nitrogen pressure, through a sterile filter,
 e) followed by filling the solution into clean, sterile, depyrogenated glass ampoules or vials, purging the ampoules with nitrogen, followed by sealing the ampoules; optionally
 f) followed by a further sterilization in form of a heat treatment.

In still another aspect of the invention, the composition according to the invention and as described herein above can be used in the control or prevention of infectious diseases, particularly in the control of bacterial infections, particularly in the control of Gram-positive strains, multi-drug-resistant Gram-positive strains, Gram-negative strains, pneumocystidaceae, parasites and opportunistic pathogens.

In one embodiment, a composition according to the invention and as described herein above is provided for use in the control or prevention of infectious diseases, particularly in the control of bacterial infections, particularly in the control of Gram-positive strains, multi-drug-resistant Gram-positive strains, Gram-negative strains, pneumocystidaceae, parasites and opportunistic pathogens.

In one embodiment of the invention, a method is provided for the control or prevention of infectious diseases, particularly for the control of bacterial infections, particularly for the control of Gram-positive strains, multi-drug-resistant Gram-positive strains, Gram-negative strains, pneumocystidaceae, parasites and opportunistic pathogens comprising administering parenterally the composition according to the present invention in a pharmaceutically effective amount to a patient in need of such a treatment.

In one embodiment of the invention administration is accomplished by i.v. bolus injection or by infusion.

In the following, specific aspects of the invention will be explained in more detail and specific examples will be provided of compositions according to the invention, which only serve to further illustrate the invention but are not to be considered limiting in any way.

Within the scope of the present invention various standard aqueous formulations of 5-[(2RS)-2-cyclopropyl-7,8-dimethoxy-2H-1-benzopyran-5-ylmethyl]-pyrimidine-2,4-diamine and its acid addition salts were tested for long term stability. For example, vials of 5-[(2RS)-2-cyclopropyl-7,8-dimethoxy-2H-1-benzopyran-5-ylmethyl]-pyrimidine-2,4-diamine methanesulfonic acid salt were prepared in 30% propylene glycol in water at a concentration of iclaprim of 20 mg/mL.

In order to examine the stability of the above standard formulations a model system was used to simulate long term storage conditions. In this model system, the solutions to be tested are stress heated at 40° C. and 70° C. for at least 12 days.

Further stability tests of the above standard formulations were performed, wherein the pH was adjusted with citric acid below 3.5 under simulated sterilization conditions, such as 100° C. for 2 h.

The analysis of the solutions after completion of the heating step were made by means of methods well known to those skilled in the art such as, for example, HPLC measurements.

Under these model conditions, the tested standard formulations showed severe stability problems. The HPLC analysis further revealed new peaks representing degradation products of the iclaprim compound.

By reducing the amount of propylene glycol and by keeping the pH above 4.0 the degradation of the iclaprim compound could be reduced, however the maximal solubility achieved for 5-[(2RS)-2-cyclopropyl-7,8-dimethoxy-2H-1-benzopyran-5-ylmethyl]-pyrimidine-2,4-diamine methanesulfonic acid salt in saline solution was only 7.5 mg/mL in comparison to the 20 mg/mL defined previously.

These findings made by using the above described model system by applying a mild stress heating allow the conclusion that long time storage at room temperature may lead to the formation of precipitations or by-products depending on the ingredients used.

Further, a color change of the solution was observed during simulated sterile lab-scale tests at lower pH, which led to the assumption that these standard formulations are sensitive under these conditions and should therefore not be terminally sterilized.

It was, therefore, an objective of the present invention to provide an improved formulation which guarantees long term stability for storage without precipitation of the parent compound or the formation of by-products, which is stable to short-term exposure of high temperatures to allow heat sterilization.

The concept implies the production of a concentrated solution of 5-[(2RS)-2-cyclopropyl-7,8-dimethoxy-2H-1-benzopyran-5-ylmethyl]-pyrimidine-2,4-diamine acid addition salt in a suitable container such as, for example, an ampoule or a vial, which may be used as such for i.v. bolus injection or, prior to use, may be diluted with an appropriate injectable solution. The concept further implies the provision of a concentrate solution wherein the components comprised therein are stable for an extended period of time and which can be conditioned in containers such as vials or ampoules which have the advantage of easy storage and shipping.

Within the scope of the present invention it was now surprisingly found that the above concept can be realized by excluding or substantially excluding oxygen from the concentrated solution and/or the headspace which is superimposed on the solution in a closed container.

Elimination of oxygen from solutions can be achieved by methods well known to those skilled in the art. In a specific embodiment of the invention, an aqueous solution of iclaprim consisting essentially of a physiologically acceptable solvent and a 5-[(2RS)-2-cyclopropyl-7,8-dimethoxy-2H-1-benzopyran-5-ylmethyl]-pyrimidine-2,4-diamine (iclaprim) acid addition salt may be purged with nitrogen until the oxygen concentration is 0.8 ppm or less in the solution and less than 5% (v/v), particularly less than 4% (v/v), but especially less than 3% (v/v) in the headspace superimposed on the solution in a closed container.

The stability of the solution can be further increased by adjusting the pH of the solution to a range of between pH 4.0 and pH 5.9, particularly in a range of between pH 4.2 and pH 5.7, particularly in a range of between pH 4.4 and pH 5.5, particularly in a range of between pH 4.6 and pH 5.2, particularly in a range of between pH 4.8 and pH 5.0, but especially in a range of between pH 4.8 and pH 5.2.

To adjust the pH within the range indicated above a physiologically acceptable acid may be added to the solution. Any physiologically acceptable acid may be used for adjusting and maintaining the pH in the desired range, particularly in a range from about 4.0 to 4.5, such as, for example, an inorganic mineral acid including a hydrochloric, a hydrobromic, a hydroiodic, a sulphuric, a nitric, a phosphoric acid and the like, or an organic sulfonic acid including alkyl- and arylsulfonic acid such as a methane- or ethane-sulfonic acid, a p-toluenesulfonic acid, a benzenesulfonic acid and the like, or a carboxylic acid including an acetic acid, a L-tartaric acid, a maleic acid, a citric acid, a benzoic acid, a salicylic acid, an ascorbic acid, a D,L-lactic acid, a L-lactic acid, a D-lactic acid, a diglycolic acid, a fumaric acid, a gentisic acid, a malonic acid, an oxalic acid, and the like. Further can be used an acidic physiologically acceptable buffer solution such as, for example, a chloride buffer, an acetate buffer, a phosphate buffer and the like.

For adjusting and maintaining the pH in a range from about 4.5 to about 5.9 a physiologically acceptable alkalinizing agent may be added to the solution such as, for example, sodium hydroxide, a mono, di- or triethanolamine or the like. In the alternative, a physiologically acceptable buffer solution may be added to the solution such as, for example, a phosphate buffer, a TRIS buffer or the like.

In one embodiment, the composition according to the present invention thus comprises a stable aqueous solution of iclaprim consisting essentially of a physiologically acceptable solvent and a 5-[(2RS)-2-cyclopropyl-7,8-dimethoxy-2H-1-benzopyran-5-ylmethyl]-pyrimidine-2,4-diamine (iclaprim) acid addition salt and a pH adjusting agent which maintains the pH in a range of between about pH 4.2 to about pH 5.7, wherein said solution is free or essentially free of oxygen.

In one embodiment, the composition according to the present invention and as described herein before comprises a stable aqueous solution of iclaprim consisting essentially of a physiologically acceptable solvent and a 5-[(2RS)-2-cyclopropyl-7,8-dimethoxy-2H-1-benzopyran-5-ylmethyl]-pyrimidine-2,4-diamine (iclaprim) or its acid addition salt in a concentration of between 0.1% (w/w) and 10% (w/w), particularly in a concentration range of between 0.2% (w/w) and 8% (w/w), particularly in a range of between 0.3% (w/w) and 5% (w/w), particularly in a range of between 0.5% (w/w) and 3% (w/w), particularly in a range of between 0.6% (w/w) and 2% (w/w), particularly in a range of between 0.8% (w/w) and 1.8% (w/w), but especially in a range of between 1% (w/w) and 2% (w/w).

The iclaprim compound may be present in the composition according to the present invention in form of any pharmaceutically acceptable acid addition salt provided that it shows a solubility in water comparable to that of the methanesulfonic acid addition salt such as, for example, an addition salt selected from the group of mineral acids, organic sulfonic acids and organic carboxylic acid, separately and mixtures thereof.

In particular, a mineral acid may be used as the acid addition salt selected from the group consisting of hydrochloric acid, hydrogen bromide, hydrogen iodide, sulphuric acid, nitric acid, phosphoric acid and the like.

Suitable organic sulfonic acid addition salts are, for example, those selected from the group consisting of alkyl- and arylsulfonic acids such as methanesulfonic acid, p-toluene-sulfonic acid, benzenesulfonic acid and the like.

A carboxylic acid addition salt that may be used within the scope of the invention is one selected from the group consisting of acetic acid, tartaric acid, maleic acid, citric acid, benzoic acid, salicylic acid, ascorbic acid and the like.

Further, any solvent which is physiologically acceptable and capable of dissolving iclaprim may be used in the composition according to the invention. Suitable solvents are, for example, water, alcohol, particularly an alcohol selected from the group consisting of ethanol, isopropanol, benzyl alcohol and the like, glycols such as propylenglycol and polyglycols, particularly a polyglycol selected from the group consisting of polyethylene glycol (PEG 300, 400, 600, 2000, 3350, 8000 . . . ), polypropylene glycol, and the like, polyalcohols such as glycerin, esters of polyalcohols such as diacetine, triacetine and the like, sugar alcohols, particularly those selected from the group consisting of mannitol, xylitol, sorbitol, and the like.

Further, a physiological saline may be used, particularly a saline solution selected from the group consisting of injectable water, full electrolyte solution containing or not amino acids, lipids, vitamins, traces elements and other minerals, Ringer-lactate solutions, Ringer-acetate solutions, sodium chloride solutions isotonic, hypotonic or hypertonic, and the like, aliphatic amides such as N-hydroxy-2 ethyl-lactamide, N,N-dimehtylacetamide, and the like.

Solubility of iclaprim and/or its acid addition salt may be further improved by the addition of additional co-solubilizing agents such as, for example wetting agents, selected from the group consisting of N-methylpyrrolidone, polyvinylpyrrolidones: Povidone 12 PF, Povidone 17 PF, Povidone 25, Povidone 30, Povidone 90 F, cyclodextrine esp. 2-hydroxypropyl-β-cyclodextrin, macrogol hydroxystearate, macrogol glycerol ricinoleate, and the like.

In one aspect of the invention, a concentrated stock solution is prepared by dissolving the iclaprim acid addition salt, particularly the iclaprim methanesulfonic acid addition salt, in water or alcohol or in a mixture thereof. In particular, mixtures of water/ethanol or water/propylene glycol, particularly a mixture containing from about 100% to about 40%, particularly from about 95% to about 55%, particularly from about 80% to about 65%, by volume of water may be used.

In particular, a mixture comprising between 27% and 34% (wt/wt) ethanol and between 73% and 66% (wt/wt) water, preferred between 29% and 31% (wt/wt) ethanol and between 71% and 69% (wt/wt) water, but especially a mixture comprising 30.6% (wt/wt) ethanol and 69.4% (wt/wt) water may be used.

This stock solution may be complemented by adding a tonicity adjustment agent such as, for example, a physiologically acceptable inorganic chloride, dextrose, lactose, mannitol and the like. In particular, sodium chloride may be used for adjusting the tonicity of the stock solution.

The pH of this stock solution may then be adjusted to a pH in the range of between 4.2 and 5.7, particularly to a pH in the range of between 4.8 and 5.2, particularly to a pH of 5.0, by adding a base to the stock solution. In particular, sodium hydroxide, particularly a 0.1 N sodium hydroxide solution, may be used for adjusting the pH of the stock solution.

To improve the solubility of 5-[(2RS)-2-cyclopropyl-7,8-dimethoxy-2H-1-benzopyran-5-ylmethyl]-pyrimidine-2,4-diamine methanesulfonic acid salt in water or a water/alcohol mixture, the stock solution may be further complemented by the addition of a solubilising or wetting agent such as, for example, an agent selected from the group consisting of N-methylpyrrolidone, polyvinylpyrrolidones (Povidone 12 PF, Povidone 17 PF, Povidone 25, Povidone 30, Povidone 90 F), cyclodextrine, esp. 2-hydroxypropyl-β-cyclodextrin, macrogol hydroxystearate, macrogol glycerol ricinoleate, and the like.

In particular, a polyvinylpyrrolidone such as Povidone 12 PF (Povidone) may be used as a wetting agent in the stock solution according to the invention.

The oxygen concentration of the stock solution is 0.8 ppm or less. This can be achieved by standard procedures known in the art commonly used to generate oxygen free solutions (e.g. osmotic membranes), or by using nitrogen-gassed water as a solvent for the iclaprim acid addition salt, or by purging the stock solution with nitrogen, particularly during the filling and sealing of the stock solution into containers for transport and storage.

In one aspect of the invention, the above described stock solution is sterilized, particularly by passing the solution as described herein through a sterile filter.

In another aspect of the invention, sterilization of the composition according the invention is accomplished by subjecting the solution to high temperatures, particularly to a temperature of between 100° C. and 175° C., particularly between 115° C. and 160° C., and high pressure, particularly to a pressure in the range of between 997 mbar and 2900 mbar particularly of between 1600 mbar and 2500 mbar for a defined period of time, particularly for a period of time in the range of between 5 minutes and at least 2 hours, particularly of between 10 minutes and 30 minutes.

Sterilization of the stock solution may also be accomplished by subjecting the solution to a combined sterile filtration and a high temperature/high pressure regime as described above.

In particular, the solution may be passed under 1 to 2 bar nitrogen pressure through a previously sterilized filter with a nominal pore size of 0.2 μm into a cleaned sterilized container. The so sterilized solution (about 5.3 mL) may then be filled into clean, sterile, depyrogenated glass ampoules of an appropriate size, the ampoules purged with nitrogen, cut and sealed.

The ampoules may then be subjected to heat sterilized at 121° C. for 15 minutes.

The so prepared ampoules can then be stored for an extended period of time under room temperature, particularly for at least 24 month.

This stock solution may be used to prepare ready-to-use injection solutions for parenteral administration or ready-to-use infusion solutions for infusion. The ready-to-use injection solution may be prepared by using the stock solution as such. The ready-to-use infusion solution may be prepared by diluting the stock solution to a desired volume by adding injectable water, glucose solutions, full electrolyte solution containing or not amino acids, lipids, vitamins, traces elements and other minerals, Ringer-lactate solutions, Ringer-acetate solutions, sodium chloride solutions isotonic, hypotonic or hypertonic, and the like either individually or in various combinations.

The composition according to the invention may then be used in the control or prevention of infectious diseases, particularly in the control of bacterial infections, particularly in the control of Gram-positive strains, multi-drug-resistant Gram-positive strains, Gram-negative strains, pneumocystidaceae, parasites and opportunistic pathogens by administering parenterally the composition according to the present invention in a pharmaceutically effective amount to a patient in need of such a treatment. Parenteral administration of the composition according to the invention may be accomplished by by i.v. bolus injection or by infusion.

In a specific embodiment, the composition of the invention as described herein before may be used in combination with a further antibacterial compound, particularly a antibacterial compound that acts as an inhibitor of enzymes which are involved in folic acid biosynthesis, particularly a compound that exhibits a synergistic effect when administered in combination with iclaprim, particularly a sulfonamide or a pteridine derivative, particularly a sulfonamide selected from the group consisting of sulfamethoxazole, sulfisoxazole, sulfadimethoxine, dapsone.

Co-administration of the further antibacterial compound may occur at the same time as the administration of the aqueous pharmaceutical composition according to the invention, either as part of the same composition or in form of a separate composition. Alternatively, the further antibacterial compound may be administered either prior or after the administration of the aqueous pharmaceutical composition according to the invention.

The following examples and the results described therein in detail illustrate how the development of an aqueous pharmaceutical composition advanced. The experiments are illustrating the invention but are not intended to limit the scope thereof.

EXAMPLES

A. Chemicals and Equipment Used in the Examples

Chemicals:

| | |
|---|---|
| Acetonitrile | Biosolve HPLC grade |
| Formic acid | Fluka purum |
| Hydrochloric acid | 32%, Fluka puriss, p.a. |
| Citric acid | Fluka puriss, p.a. |
| Propylene glycol | Fluka puriss, p.a. |
| Glycofurol 75 | Roche |

Equipment
High pressure gradient HPLC system
Waters Alliance
HPLC column Supelco Discovery C18
Heating chamber Salvis B. Detection Methods HPLC Measurements

| | |
|---|---|
| Column: | Supelco Discovery C18 |
| Column temperature: | room temperature |
| Eluent A: | 10 mM formic acid |
| Eluent B: | acetonitrile |
| Gradient: | 80% A to 20% in 10 min |
| | 20% A for 5 min |

-continued

| | |
|---|---|
| | 20% A to 80% A in 5 min |
| Injection volume: | 10 μl |
| Detection wavelength: | 254 nm |
| Flow: | 0.5 mL/min |

Method to Determine the Amount of Oxygen in the Head Space or in the Solution:

Determination of Oxygen Content in Solution:

The oxygen content in solution is measured by an amperometric determination with an oxymeter:

Calibration:—place probe in air calibration beaker containing a moist sponge start measurement; check admissible range for relative slope of the probe is correct Set measurement mode dissolved oxygen concentration (mg/L)

Determination of Oxygen Content in Headspace:

The oxygen content in the ampoule headspace is measured with a special headspace oxygen analyzer designed to measure oxygen in pharmaceutical packages.

For this purpose the ampoule is fastened to the package support and the bottom of the ampoule is cut out with a diamond tipped pencil. Degassed water is added into the ampoule and the content of oxygen is measured with an amperometric probe that has been previously calibrated.

Example 1

Preparation and Testing of a Standard Formulation for Iclaprim

Vials of 5-[(2RS)-2-cyclopropyl-7,8-dimethoxy-2H-1-benzopyran-5-ylmethyl]-pyrimidine-2,4-diamine methanesulfonic acid salt (20 mg/mL) were prepared in 30% propylene glycol in Millipore water under normal atmosphere.

In order to examine the stability of the above formulation a model experiment was developed wherein the solutions to be tested are stress heated. It is well know in the art that by heating a test sample at a temperature higher than room temperature (about 20° C.) such as between 40° C. and 70° C. for a prolonged period of time, long storage conditions can be simulated. The analysis of the solutions after completion of the heating step was made by means of visual examinations and HPLC measurements.

In Table 1 the results of a representative experiment are shown.

TABLE 1

Result of stress heating of stock solutions (20 mg/mL)

| | Duration | | | |
|---|---|---|---|---|
| | 0 min Fresh solution | 12 days | 12 days | 45 days |
| Temperature | about 20° C. | 70° C. | 40° C. | about 20° C. |
| % iclaprim | 99.1 | 90.0 | 97.0 | 97.5 |

From the results in Table 1 it can be concluded that such a formulation was not suited for long term storage, as the amount of active ingredient is decreasing over time.

Example 2

Studies of the Stability of Iclaprim under Simulated Sterilization Conditons at pH<3.5

Vials of 5-[(2RS)-2-cyclopropyl-7,8-dimethoxy-2H-1-benzopyran-5-ylmethyl]-pyrimidine-2,4-diamine methanesulfonic acid salt were prepared in 30% propylene glycol or 10% glycofurol in water.

The pH of the so obtained solution was adjusted to pH 3 with 1M citric acid or to pH 1 with 1N hydrochloric acid, and the vials were heated in order to simulate a sterilization process.

The analysis of the solutions after completion of the heating step was performed by means of visual examinations and HPLC measurements.

Representative results are shown in Table 2

TABLE 2

Studies of the stability of iclaprim under simulated sterilization conditions

| | Duration of the treatment | | | | | |
|---|---|---|---|---|---|---|
| | 0 min Fresh solution | 1 h | 3 h | 2 h | 3 h | 2 h |
| | | | | Temperature | | |
| | about. 20° C. | 37° C. | 37° C. | 100° C. | 37° C. | 100° C. |
| pH of the solution | 4.5* | 1 | 1 | 1 | 3 | 3 |
| % iclaprim | 99.1 | 99.0 | 96.3 | 60.0 | 99.0 | 86.5 |

*pH of reference solution without adjustment of pH

From the results in Table 2 it can be concluded that such a formulation at pH 3 or less was not suited for heat sterilization, as the amount of active ingredient is decreasing over time.

Example 3

Solubility of Iclaprim Methanesulfonic Acid Salt

The solubility of iclaprim mesylate in different aqueous/organic solution was studied and is presented in table 3. A fixed amount of iclaprim mesylate was suspended in the different aqueous/organic solutions. The suspension was stirred at room temperature for 24 hours. The supernatant of the solutions were analyzed by HPLC to determine the amount of iclaprim in the solution.

Representative results are presented in Table 3.

TABLE 3

Solubility of iclaprim methanesulfonic acid salt

| Solution | Solubility calculated form HPLC measurements (mg/mL) |
|---|---|
| water | 18.1 |
| Saline 0.9% | 1.2 |
| 10% aqueous propylene glycol | 27.8 |
| 10% (saline 0.9%) propylene glycol | 7.5 |

Example 4

Preparation of a Stock Solution

Water for injection (10 parts vol/vol), Povidone 12 PF (2 parts), sodium chloride (0.2 parts) and ethanol (7.5 parts) were stirred until complete solution in a stainless steel mixing tank under a continuous flow of nitrogen. The solution was permanently controlled to ensure that the content of residual oxygen in the solution is less than 0.8 ppm.

Subsequently, 5-[(2R,S)-cyclopropyl-7,8-dimethoxy-2H-1-benzopyran-5-ylmethyl]-pyrimidine-2,4-diamine methanesulfonic acid salt (0.4 parts) was added to the solution and stirred until complete dissolution. The pH of the solution was then adjusted with 0.1 N sodium hydroxide solution to a value between pH 4.8 to 5.2. The volume of the solution was adjusted to arrive at a final concentration of 1.28% iclaprim.

In a closed system, the so obtained solution was filtered though a sterile filter with a nominal pore size of 0.2 μm with a 1 to 2 bar nitrogen streem. Appropriately sized, clean, sterile, depyrogenated glass ampoules were filled with the filtered solution under aseptic conditions and a nitrogen atmosphere, purged with nitrogen by flushing the solution with a 1 to 2 bar nitrogen stream and sealed with constriction under a flame.

A further sterilization step may be applied by treating the ampoules by heat at 121° C. for 15 minutes.

The content of such an ampoule can be diluted with saline to give a stable solution ready for a large volume i.v. infusion.

Example 5

Stability Testing

Example 5.1

A sealed ampoule (total volume of the ampoule between 6.5 mL and 5.5 mL) was prepared as described in Example 4 above to contain a stock solution (total volume of 5.3 mL) by purging the ampoule with nitrogen during filling in order to keep the amount of oxygen in the headspace lower than 3% v/v. The sterilization by heat treatment according to step 11 was not performed.

The ampoule was opened and immediately analysed by HPLC using the method described above.

Example 5.2

A sealed ampoule such as the one described in example 5.1 was subjected to the additional sterilization by heat treatment at 121° C. for 15 minutes as described in step 11 of Example 4.

The ampoule was opened and immediately analysed by HPLC using the method described above.

Example 5.3

A sealed ampoule such as the one in example 5.1 was opened and the solution was refilled in another empty ampoule under normal air conditions (containing ca. 20% oxygen).

The solution so obtained was analysed by HPLC using the method described above.

Example 5.4

A sealed ampoule such as the one in example 5.1 was opened and the solution was refilled into another empty ampoule under normal air conditions (containing ca. 20% oxygen).

The ampoule was subjected to additional sterilization by heat treatment at 121° C. for 15 minutes as described in step 11 of Example 4.

The ampoule was opened and immediately analysed by HPLC using the method described above.

Representative results are presented in table 4.

TABLE 4

Stability of iclaprim concentrate solution (stock solution) under controlled amounts of oxygen

| Example | Oxygen in headspace % (v/v) | Color* | Impurity** 1 | Impurity 2 | Impurity 3 |
|---|---|---|---|---|---|
| 5.1 | 0.26 | BY6 | 0.11 | 0.08 | 0.12 |
| 5.2 | 0.18 | BY5 | 0.08 | 0.08 | 0.18 |
| 5.3 | 9.38 | BY5 | 0.18 | 0.13 | 0.18 |
| 5.4 | 5.43 | BY4 | 0.26 | 0.19 | 0.33 |

*European Pharmacopoeia 4, 2.2.2 Degree of coloration of liquids, pp 23-24
**HPLC Chromatographic conditions to identify impurity 1, 2 and 3

| | |
|---|---|
| Column: | YMC ODS-AQ, 250 × 4.6 mm, 5 μm |
| Column Temp.: | 40° C. |
| Mobile Phase A: | $H_3PO_4$ 0.1% |
| Mobile Phase B: | MeOH |
| Mobile Phase C: | $CH_3CN$ |

| Time (min) | % A | % B | % C |
|---|---|---|---|
| 0 | 75 | 15 | 10 |
| 15 | 60 | 15 | 25 |
| 30 | 10 | 15 | 75 |
| 35 | 10 | 15 | 75 |

| | |
|---|---|
| Flow: | 1 mL/min |
| Post run | 10 minutes |
| Detector | UV at 230 nm |
| Injection volume: | 10 μL |
| Run time | 35 minutes |
| Diluent | Water/MeOH/$CH_3CN$ 6/2/2 v/v/v |

The observed impurities 1, 2 and 3 are degradation products due to oxidation of iclaprim:
iclaprim: $[M+H]^+$=355, HPLC retention time: 6.1
Impurity 1: $[M+H]^+$=353, HPLC retention time: 9.2
Impurity 2: $[M+H]^+$=371, HPLC retention time: 3.8
Impurity 3: $[M+H]^+$=389, HPLC retention time: 3.3

The result of Example 5.4 demonstrates that exposition of the samples to air (containing about 20% oxygen) causes a significant change in color (BY6 to BY4) as well as decrease of active ingredient and/or a considerable increase of degradation products after autoclavation. Unopened samples only showed a slight change in color (BY6 to BY5) after autoclavation (Example 5.2). The result of Example 5.3 demonstrates that vials can be opened and handled under normal atmosphere without affecting the stability of the solution.

The invention claimed is:
1. A composition comprising a 5-[(2RS)-2-cyclopropyl-7,8-dimethoxy-2H-1-benzopyran-5-ylmethyl]-pyrimidine-2,4-diamine (iclaprim) in a solution consisting essentially of a physiologically acceptable solvent and a 5-[(2RS)-2-cyclopropyl-7,8-dimethoxy-2H-1-benzopyran-5-ylmethyl]-pyri- midine-2,4-diamine (iclaprim) addition salt characterized in that the oxygen concentration in the solution is 0.8 ppm or less.

2. The composition according to claim 1, wherein the physiologically acceptable solvent is selected from the group consisting of water, alcohol, a physiological saline, an aliphatic amide, a glycol, a polyalcohol, esters of a polyalcohol, polyglycols, polyethers, and sugar alcohols or mixtures thereof.

3. The composition according to claim 2, wherein the physiologically acceptable solvent is water or ethanol or a water/ethanol mixture.

4. The composition according to claim 3 comprising ethanol in a concentration range of between 0% and 50%.

5. The composition according to claim 3 comprising ethanol in a concentration range of between 5% and 45%.

6. The composition according to claim 3 comprising ethanol in a concentration range of between 20% and 35%.

7. The composition according to claim 1 further comprising natrium chloride (NaCl) in a concentration of between 0% and 3%.

8. The composition according to claim 1 further comprising natrium chloride (NaCl) in a concentration of between 0.1% and 1%.

9. The composition according to claim 1, wherein the pH of the solution is in a range of between pH 4.2 and pH 5.7.

10. The composition according to claim 1, wherein the concentration of the 5-[(2RS)-2-cyclopropyl-7,8-dimethoxy-2H-1-benzopyran-5-ylmethyl]-pyrimidine-2,4-diamine (iclaprim) in the solution is in a range of at least 0.1% (w/w).

11. The composition according to claim 1, wherein the concentration of the 5-[(2RS)-2-cyclopropyl-7,8-dimethoxy-2H-1-benzopyran-5-ylmethyl]-pyrimidine-2,4-diamine (iclaprim) in the solution is in a range of at least 1% and not exceeding 2%.

12. The composition according to claim 1 further comprising a wetting agent, selected from the group consisting of N-methylpyrrolidone, polyvinylpyrrolidone, cyclodextrine, macrogol hydroxystearate, and macrogol glycerol ricinoleate in a concentration of between 0% and 20%.

13. The composition according to claim 1 further comprising a wetting agent selected from the group consisting of N-methylpyrrolidone, polyvinylpyrrolidone, cyclodextrine, macrogol hydroxystearate, and macrogol glycerol ricinoleate in a concentration of between 0.1% and 10%.

14. The composition according to claim 1 wherein the addition salt is an acid addition salt selected from the group of salts consisting of a salt with a mineral acid, an organic sulfonic acid and an organic carboxylic acid, separately and mixtures thereof.

15. The composition according to claim 1 wherein the addition salt is a methanesulfonic acid addition salt.

16. The composition according to claim 1, further comprising a biologically active agent or compound.

17. The composition according to claim 16, wherein the biologically active agent or compound is a sulfonamide selected from the group consisting of sulfamethoxazole, sulfisoxazole, sulfadimethoxine, dapsone.

18. A container having therein the composition according to claim 1, wherein the container is a sealed container such as a vial or an ampoule, and wherein said composition comprises a physiologically acceptable solution and the oxygen concentration in the headspace is less than 5% (v/v).

19. The composition according to claim 1 for use in the control or prevention of infectious diseases in humans or animals.

20. The composition according to claim 19, for use in the control or prevention of bacterial infections.

21. The composition according to claim 20, for use in the control or prevention of Gram-positive strains, multi-drug-resistant Gram-positive strains, Gram-negative strains, pneumocystidaceae, parasites and opportunistic pathogens.

* * * * *